US012558044B2

(12) United States Patent
Nishijima

(10) Patent No.: US 12,558,044 B2
(45) Date of Patent: Feb. 24, 2026

(54) PHOTON COUNTING CT APPARATUS AND METHOD OF CONTROLLING PHOTON COUNTING CT APPARATUS

(71) Applicant: CANON MEDICAL SYSTEMS CORPORATION, Otawara (JP)

(72) Inventor: Akira Nishijima, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 82 days.

(21) Appl. No.: 18/593,329

(22) Filed: Mar. 1, 2024

(65) Prior Publication Data

US 2024/0293094 A1 Sep. 5, 2024

(30) Foreign Application Priority Data

Mar. 2, 2023 (JP) ................................. 2023-032083

(51) Int. Cl.
*A61B 6/42* (2024.01)
*A61B 6/03* (2006.01)

(52) U.S. Cl.
CPC ............ *A61B 6/4241* (2013.01); *A61B 6/035* (2013.01); *A61B 6/4233* (2013.01)

(58) Field of Classification Search
CPC ........... A61B 6/03; A61B 6/032; A61B 6/585; A61B 6/4241; A61B 6/4233
See application file for complete search history.

(56) References Cited

U.S. PATENT DOCUMENTS

2021/0219930 A1 7/2021 Tsuchiya et al.

FOREIGN PATENT DOCUMENTS

JP 2021-112464 A 8/2021
WO WO-2018163782 A1 * 9/2018 ............. G01T 1/244

* cited by examiner

*Primary Examiner* — Don K Wong
(74) *Attorney, Agent, or Firm* — Oblon, McClelland, Maier & Neustadt, L.L.P.

(57) ABSTRACT

A photon counting CT apparatus of an embodiment has a detector module including a semiconductor detector and first processing circuitry configured to process detection data detected by the semiconductor detector. The first processing circuitry is configured to generate heat by performing a pseudo operation during a period in which X-ray exposure is stopped.

10 Claims, 6 Drawing Sheets

(A) ABSENCE OF PSEUDO OPERATION (CONVENTIONAL)

DETECTOR TEMPERATURE

IDLE STATE          SCAN          IDLE STATE (B) PRESENCE OF PSEUDO OPERATION

DETECTOR TEMPERATURE

PSEUDO OPERATION          SCAN          PSEUDO OPERATION

CONSOLE DEVICE          40

DETECTOR MODULE          20

S101
DETERMINE PSEUDO OPERATION

TRANSMIT PSEUDO OPERATION CONTROL SIGNAL

S103

S105
PSEUDO OPERATION

FIG. 6

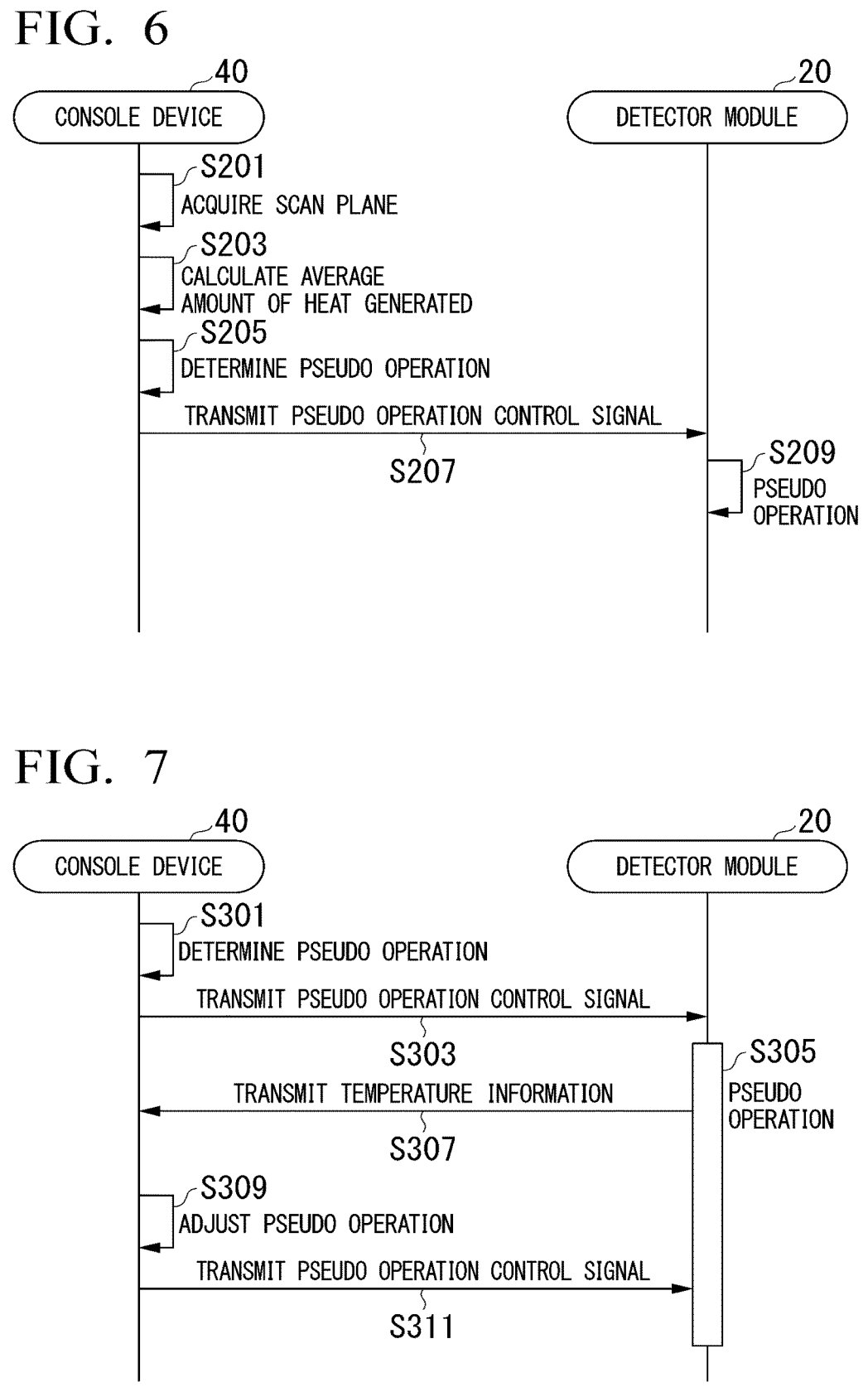

CONSOLE DEVICE _40

DETECTOR MODULE _20

S201
ACQUIRE SCAN PLANE

S203
CALCULATE AVERAGE
AMOUNT OF HEAT GENERATED

S205
DETERMINE PSEUDO OPERATION

TRANSMIT PSEUDO OPERATION CONTROL SIGNAL

S207

S209
PSEUDO
OPERATION

FIG. 7

CONSOLE DEVICE _40

DETECTOR MODULE _20

S301
DETERMINE PSEUDO OPERATION

TRANSMIT PSEUDO OPERATION CONTROL SIGNAL

S303

S305
PSEUDO
OPERATION

TRANSMIT TEMPERATURE INFORMATION

S307

S309
ADJUST PSEUDO OPERATION

TRANSMIT PSEUDO OPERATION CONTROL SIGNAL

S311

PHOTON COUNTING CT APPARATUS AND METHOD OF CONTROLLING PHOTON COUNTING CT APPARATUS

CROSS-REFERENCE TO RELATED APPLICATION

The present application claims priority based on Japanese Patent Application No. 2023-032083 filed Mar. 2, 2023, the content of which is incorporated herein by reference.

FIELD

Embodiments disclosed in this specification and the drawings relate to a photon counting CT apparatus and a method of controlling the photon counting CT apparatus.

BACKGROUND

Semiconductor detectors used in photon counting computed tomography (PCCT) apparatuses have output characteristics with a large temperature dependence and are required to be used at a constant temperature. On the other hand, in order to rapidly read detection data, it is required that the distance between a semiconductor detector and processing circuitry (an application specific integrated circuit (ASIC) or the like) be as short as possible.

Since the processing circuitry operates according to the number of X-ray photons incident on the semiconductor detector, the amount of heat generated varies during exposure or non-exposure, or depending on the number of incident photons, and the temperature of the semiconductor detector changes accordingly. In particular, temperature change in the processing circuitry from an idle time to the start of X-ray exposure is significant. In this manner, the temperature of the semiconductor detector varies depending on the situation, which may cause problems in the accuracy of detection results (image quality of generated CT images) during scanning and calibration.

BRIEF DESCRIPTION OF THE DRAWINGS

FIG. 6 is a sequence diagram showing an example of a flow of second processing (varying pseudo operation according to a scan plan) of the photon counting CT apparatus 1 according to an embodiment.

FIG. 7 is a sequence diagram showing an example of a flow of third processing (varying pseudo operation according to detector temperature) of the photon counting CT apparatus 1 according to an embodiment.

DETAILED DESCRIPTION

Hereinafter, a photon counting CT apparatus and a method of controlling the photon counting CT apparatus of an embodiment will be described with reference to the drawings.

The photon counting CT apparatus of the embodiment has a detector module including a semiconductor detector and first processing circuitry configured to process detection data detected by the semiconductor detector. The first processing circuitry is configured to generate heat by performing a pseudo operation during a period in which X-ray exposure is stopped.

Embodiment

[Configuration of Photon Counting CT Apparatus]

Figure 1:
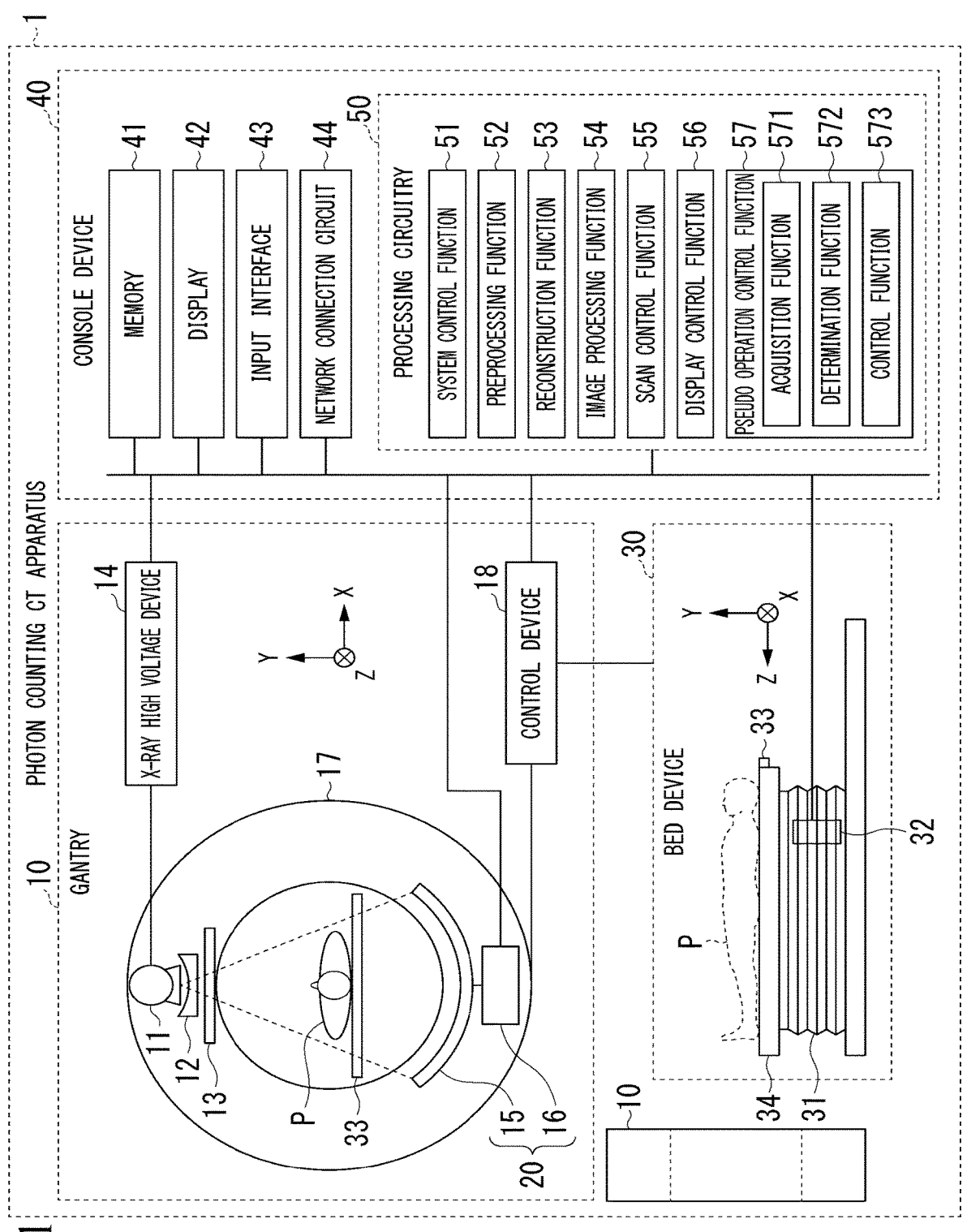
FIG. 1 is a diagram showing an example of a photon counting CT apparatus 1 according to an embodiment.

FIG. 1 is a diagram showing an example of a photon counting CT apparatus 1 according to an embodiment. The photon counting CT apparatus 1 according to the present embodiment stabilizes the temperature of a semiconductor detector by performing a pseudo operation that causes processing circuitry to operate in a pseudo manner during a non-scanning time (at the time of idle) when there is no exposure with X-rays. Note that the non-scanning time (idle time) includes both a non-scanning time when scanning a subject (main scanning) is performed and a non-scanning time when calibration is performed.

The photon counting CT apparatus 1 can generate image data that discriminates a substance to be examined through which X-rays have passed using a direct detector such as a semiconductor detector with excellent energy resolution. The photon counting CT apparatus 1 includes, for example, a gantry 10, a bed device 30, and a console device 40. The term "photon counting CT apparatus" may indicate all of the gantry 10, the bed device 30, and the console device 40, or may indicate at least one of the gantry 10, the bed device 30, and the console device 40. For convenience of description, FIG. 1 shows both a view of the gantry 10 viewed in the Z-axis direction and a view viewed in the X-axis direction, but in reality, there is only one gantry 10. In the present embodiment, a rotation axis of a rotating frame 17 in a non-tilted state or the longitudinal direction of a top plate 33 of the bed device 30 is defined as the Z-axis direction, an axis perpendicular to the Z-axis direction and horizontal to the floor surface is defined as the X-axis direction, and a direction that is perpendicular to the Z-axis direction and orthogonal to the floor surface is defined as the Y-axis direction.

[Gantry 10]

The gantry 10 includes, for example, an X-ray tube 11, a wedge 12, a collimator 13, an X-ray high voltage device 14, an X-ray detector 15, a data acquisition system (hereinafter referred to as DAS) 16, the rotating frame 17, and a control device 18. The X-ray detector 15 and the DAS 16 constitute a detector module 20.

The X-ray tube 11 generates X-rays by radiating thermoelectrons from a cathode (filament) toward an anode (target) when a high voltage from the X-ray high voltage device 14 is applied thereto. The X-ray tube 11 includes a vacuum tube. For example, the X-ray tube 11 is a rotating anode type X-ray tube that generates X-rays by radiating thermoelectrons to the rotating anode.

The wedge 12 is a filter for adjusting X-ray doses radiated from the X-ray tube 11 to a subject P. The wedge 12 attenuates X-rays that pass through the wedge 12 such that the distribution of the X-ray doses radiated from the X-ray tube 11 to the subject P becomes a predetermined distribution. The wedge 12 is also called a wedge filter or a bow-tie filter. The wedge 12 is, for example, made of aluminum processed to have a predetermined target angle and a predetermined thickness.

The collimator 13 is a mechanism for narrowing down a radiation range of X-rays that have passed through the wedge 12. The collimator 13 narrows down the radiation range of X-rays by forming a slit using a combination of a plurality of lead plates, for example. The collimator 13 is sometimes called an X-ray diaphragm. The narrowing range of the collimator 13 may be mechanically drivable.

The X-ray high voltage device 14 includes, for example, a high voltage generator that is not shown and an X-ray control device that is not shown. The high voltage generator has an electric circuit including a transformer, a rectifier, etc., and generates a high voltage to be applied to the X-ray tube 11. The X-ray control device controls the output voltage of the high voltage generator in response to X-ray doses to be generated by the X-ray tube 11. The high voltage generator may boost the voltage using the above-mentioned transformer or may boost the voltage using an inverter. The X-ray high voltage device 14 may be provided on the rotating frame 17 or may be provided on the side of a fixed frame (not shown) of the gantry 10.

The X-ray detector 15 detects the intensity of X-rays generated by the X-ray tube 11 and incident through the subject P. The X-ray detector 15 outputs an electrical signal (an optical signal or the like) corresponding to the intensity of the detected X-rays to the DAS 16. The X-ray detector 15 has, for example, a plurality of X-ray detection element rows. Each of the plurality of X-ray detection element rows has a plurality of X-ray detection elements arranged in a channel direction along an arc having the focal point of the X-ray tube 11 as a center. The plurality of X-ray detection element rows are arranged in a slice direction (column direction or row direction). The X-ray detector 15 is an example of a "semiconductor detector."

The X-ray detector 15 is, for example, a direct detection type detector. As the X-ray detector 15, for example, a semiconductor diode having electrodes attached to both ends of a semiconductor can be used. X-ray photons incident on a semiconductor are converted into electron-hole pairs. The number of electron-hole pairs generated according to incidence of one X-ray photon depends on the energy of the incident X-ray photon. Electrons and holes are attracted to a pair of electrodes formed at both ends of the semiconductor. The pair of electrodes generates electric pulses having a peak value depending on the charge of the electron-hole pairs. One electric pulse has a peak value that corresponds to the energy of the incident X-ray photon.

Figure 2:
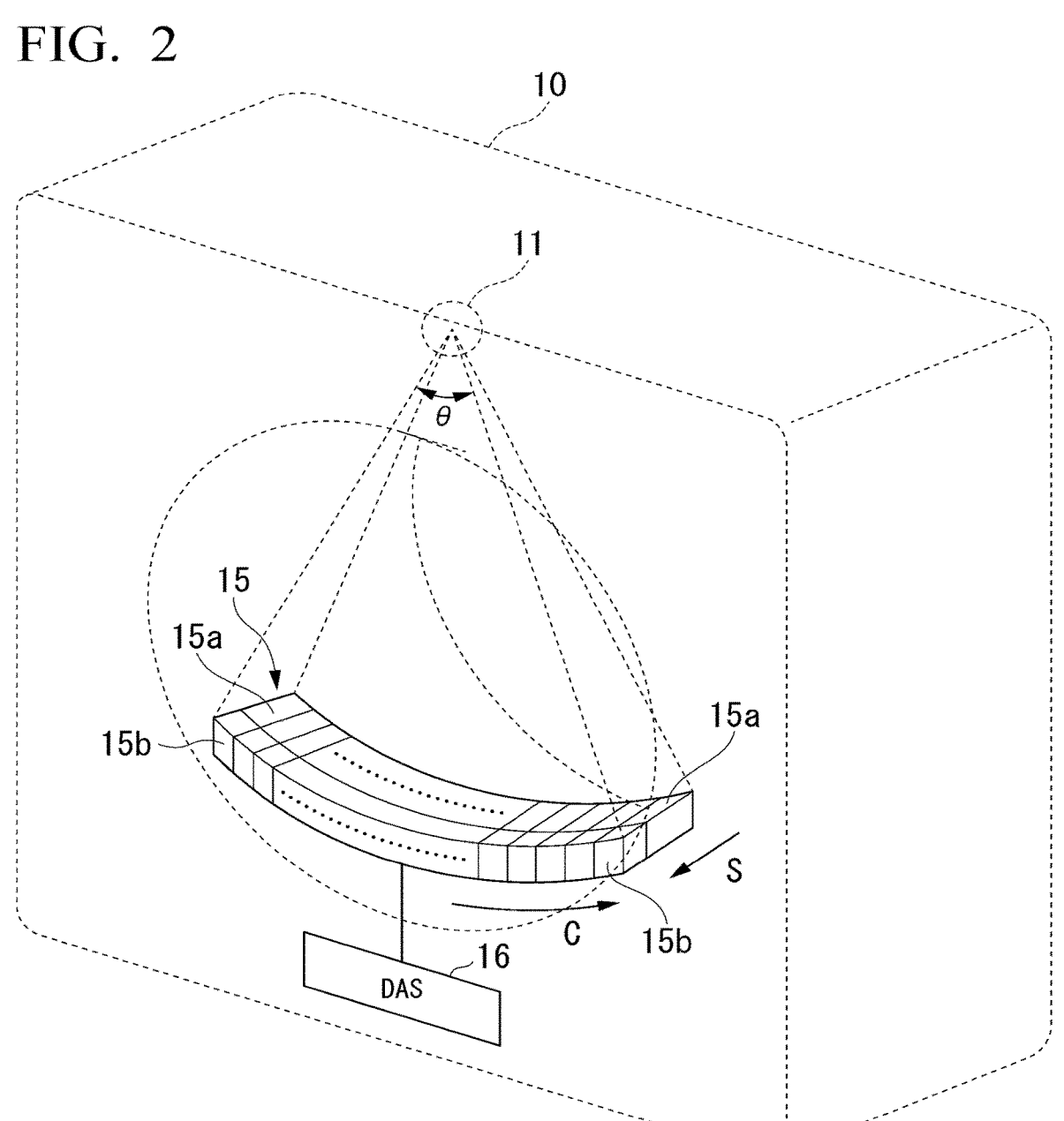
FIG. 2 is a perspective view showing an example of configurations of a gantry 10 and an X-ray detector 15 according to an embodiment.

FIG. 2 is a perspective view showing an example of the configuration of the gantry 10 and the X-ray detector 15 according to an embodiment. The X-ray detector 15 includes a plurality of detection units 15a (pack) and a temperature sensor 15b that measures the temperature of each detection unit 15a. The detection units 15a are disposed side by side in the shown channel direction C. Moreover, the temperature sensor 15b is disposed at one end of each detection unit 15a. Note that the temperature sensor 15b may be provided in the DAS 16 to measure the temperature of the DAS 16.

The DAS 16 collects count data indicating the number of counts of X-ray photons detected by the X-ray detector 15 with respect to a plurality of energy bins, for example, according to a control signal from the control device 18. The count data with respect to the plurality of energy bins corresponds to the energy spectrum regarding incident X-rays to the X-ray detector 15, which is modified according to response characteristics of the X-ray detector 15. The DAS 16 outputs detection data based on digital signals to console device 40. The detection data is a digital value of count data identified by the channel number and the column number of an X-ray detection element that is a generation source, and a view number indicating a collected view. A view number is a number that changes according to rotation of the rotating frame 17, and is a number that is incremented according to rotation of the rotating frame 17, for example. Therefore, the view number is information indicating the rotation angle of the X-ray tube 11. A view period is a period that falls between a rotation angle corresponding to a certain view number and a rotation angle corresponding to the next view number.

The DAS 16 may detect switching of views using a timing signal input from the control device 18, an internal timer, or a signal obtained from a sensor that is not shown. In a case where full scanning is performed, when X-rays are continuously exposed from the X-ray tube 11, the DAS 16 collects a group of detection data for the entire circumference (360 degrees). In a case where half scanning is performed, when X-rays are continuously exposed from the X-ray tube 11, the DAS 16 collects detection data for half the circumference (180 degrees). The DAS 16 processes detection data detected by the semiconductor detector. The DAS 16 is an example of "first processing circuitry."

Figure 3:
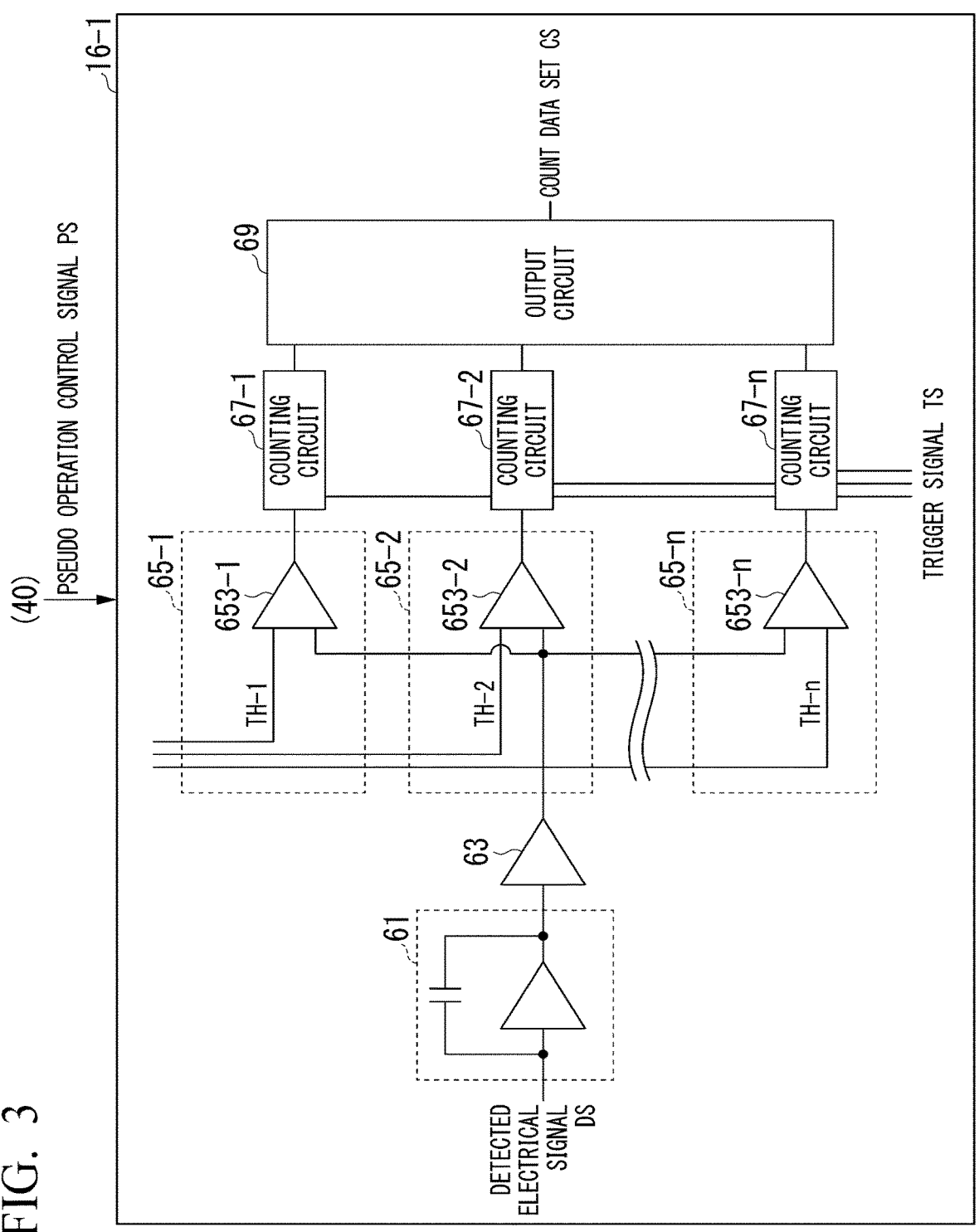
FIG. 3 is a diagram showing an example of a configuration of a DAS 16-1 according to an embodiment.

FIG. 3 is a diagram showing an example of the configuration of the DAS 16 according to an embodiment. The DAS 16 includes readout channels corresponding to the number of X-ray detection elements. Such a plurality of readout channels are implemented in parallel on an integrated circuit such as an ASIC. FIG. 3 shows only the configuration of a DAS 16-1 for one readout channel.

The DAS 16-1 includes a preamplifier circuit 61, a waveform shaping circuit 63, a plurality of pulse height discrimination circuits 65, a plurality of counting circuits 67, and an output circuit 69. The DAS 16-1 is provided with a temperature sensor (not shown) that measures the temperature of the DAS 16-1. The preamplifier circuit 61 amplifies a detected electrical signal DS (current signal) from a connected X-ray detection element. For example, the preamplifier circuit 61 converts the current signal from the connected X-ray detection element into a voltage signal having a voltage value (peak value) proportional to the amount of charge of the current signal. The waveform shaping circuit 63 is connected to the preamplifier circuit 61. The waveform shaping circuit 63 shapes the waveform of a voltage signal from the preamplifier circuit 61. For example, the waveform shaping circuit 63 reduces the pulse width of the voltage signal from the preamplifier circuit 61. The DAS 16-1 is an example of "first processing circuitry."

A plurality of counting channels corresponding to the number of energy bands (energy bins) are connected to the waveform shaping circuit 63. In a case where n energy bins are set, the waveform shaping circuit 63 is provided with n counting channels. Each counting channel has a pulse height discrimination circuit 65-n and a counting circuit 67-n.

Each pulse height discrimination circuit 65-n discriminates the energy of X-ray photons detected by the X-ray detection element, which is the peak value of a voltage signal from the waveform shaping circuit 63. For example, each pulse height discrimination circuit 65-n includes a comparison circuit 653-n. A voltage signal from the waveform shaping circuit 63 is input to one input terminal of each comparison circuits 653-n. Reference signals TH (reference voltage values) corresponding to different threshold values are supplied from the control device 18 to the other input terminals of the comparison circuits 653-*n*.

For example, a reference signal TH-1 is supplied to a comparison circuit 653-1 for an energy bin bin1, a reference signal TH-2 is supplied to a comparison circuit 653-2 for an energy bin bin2, and a reference signal TH-n is supplied to a comparison circuit 653-*n* for an energy bin binn. Each of the reference signals TH has an upper limit reference value and a lower limit reference value. Each of the comparison circuits 653-*n* outputs an electric pulse signal when the voltage signal from the waveform shaping circuit 63 has a peak value corresponding to the energy bin corresponding to each of the reference signals TH. For example, if the peak value of the voltage signal from the waveform shaping circuit 63 is a peak value corresponding to the energy bin bin1 (if it falls between the reference signals TH-1 and TH-2), the comparison circuit 653-1 outputs an electrical pulse signal. On the other hand, the comparison circuit 653-1 for the energy bin bin1 does not output an electric pulse signal if the peak value of the voltage signal from the waveform shaping circuit 63 is not a peak value corresponding to the energy bin bin1. Further, if the peak value of the voltage signal from the waveform shaping circuit 63 is a peak value corresponding to the energy bin bin2 (if falls between the reference signals TH-2 and TH-3), for example, the comparison circuit 653-2 outputs an electrical pulse signal.

The counting circuit 67-*n* counts electrical pulse signals from the pulse height discrimination circuit 65-*n* at a readout cycle that matches a view switching cycle. For example, a trigger signal TS is supplied from the control device 18 to the counting circuit 67-*n* at a switching timing of each view. In response to supply of the trigger signal TS, the counting circuit 67-*n* adds 1 to the count stored in an internal memory every time an electric pulse signal is input from the pulse height discrimination circuit 65-*n*. In response to supply of the next trigger signal, the counting circuit 67-*n* reads data of the count (i.e., count data) stored in the internal memory and supplies the count data to the output circuit 69. Further, the counting circuit 67-*n* resets the count stored in the internal memory to an initial value every time the trigger signal TS is supplied. In this manner, the counting circuit 67-*n* counts the count for each view.

The output circuit 69 is connected to counting circuits 67-*n* for a plurality of readout channels mounted on the X-ray detector 15. For each of the plurality of energy bins, the output circuit 69 integrates count data from the counting circuits 67-*n* for the plurality of readout channels to generate count data for the plurality of readout channels for each view. The count data of each energy bin is a set of count data defined by a channel, a segment (column), and an energy bin. The count data of each energy bin is transmitted to the console device 40 in units of views. Count data for each view is called a count data set CS. Furthermore, the output circuit 69 transmits data detected for each pixel detected by the X-ray detector 15 to the console device 40. The detected data includes at least one of data detected for each pixel and count data for each energy bin.

The detector module 20 performs a pseudo operation on the basis of a pseudo operation control signal PS output from the console device 40, for example. The pseudo operation refers to pseudo-operating the ASIC (DAS 16) of the detector module 20 without X-ray exposure. By performing such a pseudo operation, the detector module 20 can stabilize the temperature of the X-ray detector 15 (semiconductor detector) during non-scanning (at the time of idle) without X-ray exposure.

Figure 4:
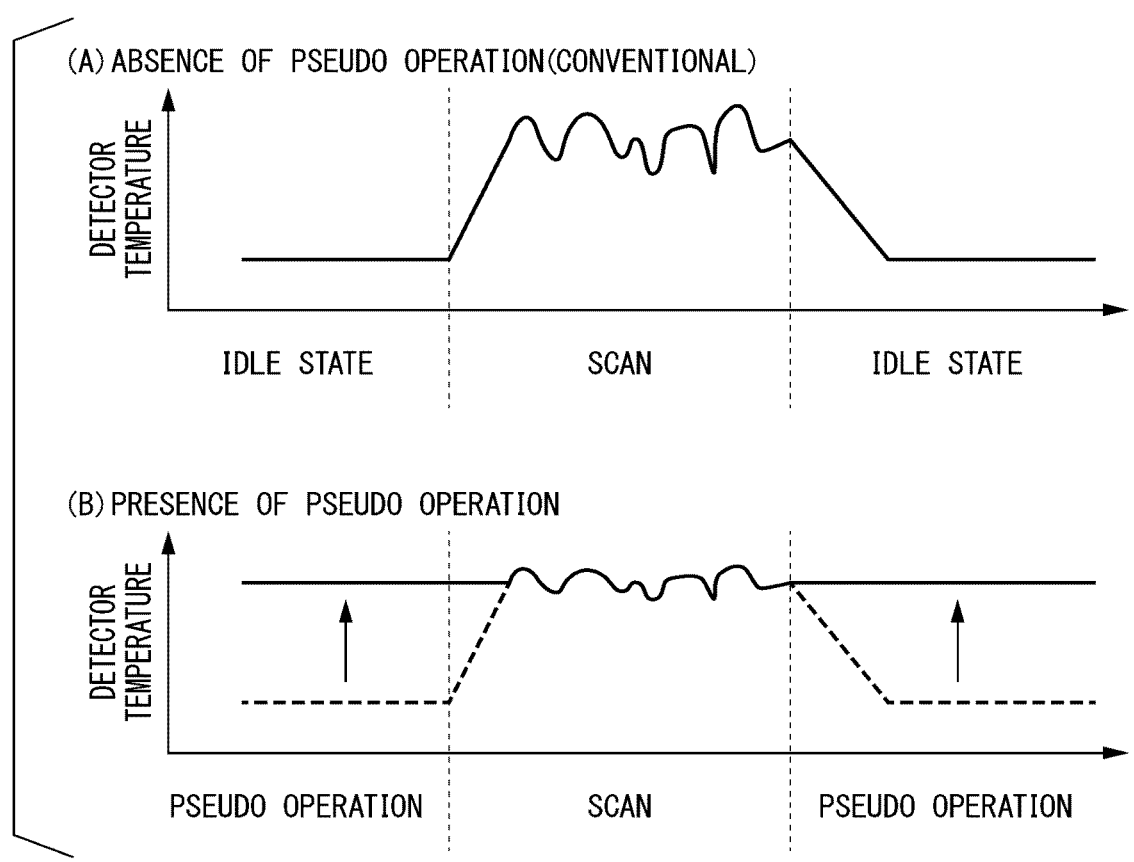
FIG. 4 is a diagram showing how the temperature changes in the X-ray detector 15 according to an embodiment.

FIG. 4 is a diagram showing how the temperature of the X-ray detector 15 changes according to an embodiment. As shown in (A) of FIG. 4, in the conventional configuration in which a pseudo operation is not performed, the temperature of the X-ray detector 15 is low because the DAS 16 does not operate during non-scanning (at the time of idle), but the DAS 16 operates and the temperature rises when scanning starts, and accordingly, the temperature of the X-ray detector 15 rises, and after scanning ends, it enters an idle state again, and the temperature of the X-ray detector 15 decreases. In this manner, in the conventional configuration, the temperature of the X-ray detector 15 fluctuates depending on conditions.

On the other hand, as shown in (B) of FIG. 4, in the present embodiment, the DAS 16 performs a pseudo operation during a period corresponding to the conventional idle time, and thus the temperature of the X-ray detector 15 is maintained high during this period as well. As a result, temperature changes in the X-ray detector 15 can be reduced at the time of idle and scanning.

Referring back to FIG. 1, the rotating frame 17 is an annular member that supports the X-ray tube 11, the wedge 12, the collimator 13, and the X-ray detector 15 in a facing manner. The rotating frame 17 is rotatably supported by a fixed frame around a subject P introduced therein. The rotating frame 17 further supports the DAS 16. Detection data output by the DAS 16 is transmitted through optical communication from a transmitter having a light emitting diode (LED) provided in the rotating frame 17 to a receiver having a photodiode provided in a non-rotating part (for example, a fixed frame) of the gantry 10 and transferred by the receiver to the console device 40. Note that the method of transmitting the detection data from the rotating frame 17 to the non-rotating part is not limited to the method using optical communication described above, and any non-contact type transmitting method may be employed. The rotating frame 17 is not limited to an annular member, and may be an arm-like member as long as it can support and rotate the X-ray tube 11 and the like.

The photon counting CT apparatus 1 is, for example, a rotate/rotate-type X-ray CT apparatus (a third generation CT), in which both the X-ray tube 11 and the X-ray detector 15 are supported by the rotating frame 17 and rotate around the subject P, but it is not limited thereto and may be a stationary/rotate-type X-ray CT device (a fourth generation CT) in which a plurality of X-ray detection elements arranged in an annular shape are fixed to a fixed frame and the X-ray tube 11 rotates around the subject P.

The control device 18 includes, for example, processing circuitry including a processor such as a central processing unit (CPU). The control device 18 receives an input signal from an input interface attached to the console device 40 or the gantry 10 and controls the operations of the gantry 10, the bed device 30, and the DAS 16. For example, the control device 18 rotates the rotating frame 17 or tilts the gantry 10. AT the time of tilting the gantry 10, the control device 18 rotates the rotating frame 17 about an axis parallel to the Z-axis direction on the basis of a tilt angle input to the input interface. The control device 18 ascertains a rotation angle of the rotating frame 17 on the basis of the output of a sensor that is not shown or the like. Further, the control device 18 controls an energy bin (reference signal TH) of the DAS 16. The control device 18 may be provided on the gantry 10 or may be provided on the console device 40.

The bed device 30 is a device on which the subject P to be scanned is placed and moved, and introduced into the rotating frame 17 of the gantry 10. The bed device 30 includes, for example, a base 31, a bed driving device 32, a top plate 33, and a support frame 34. The base 31 includes a housing that supports the support frame 34 movably in the vertical direction (Y-axis direction). The bed driving device 32 includes a motor and an actuator. The bed driving device 32 moves the top plate 33 along the support frame 34 in the longitudinal direction of the top plate 33 (Z-axis direction). Further, the bed driving device 32 moves the top plate 33 in the vertical direction (Y-axis direction). The top plate 33 is a plate-shaped member on which the subject P is placed.

The bed driving device 32 may move not only the top plate 33 but also the support frame 34 in the longitudinal direction of the top plate 33. Further, contrary to the above, the gantry 10 may be movable in the Z-axis direction, and the rotating frame 17 may be controlled to come around the subject P by moving the gantry 10. Further, both the gantry 10 and the top plate 33 may be movable. In addition, the photon counting CT apparatus 1 may be an apparatus in which the subject P is scanned in a standing or sitting position. In this case, the photon counting CT apparatus 1 has a subject support mechanism in place of the bed device 30, and the gantry 10 rotates the rotating frame 17 in an axial direction perpendicular to the floor surface.

[Console Device 40]

The console device 40 includes, for example, a memory 41, a display 42, an input interface 43, a network connection circuit 44, and processing circuitry 50. Although the console device 40 will be described as being separate from the gantry 10 in the present embodiment, the gantry 10 may include some or all of the components of the console device 40.

The memory 41 is realized by, for example, a random access memory (RAM), a semiconductor memory element such as a flash memory, a hard disk, an optical disk, or the like. The memory 41 stores, for example, detection data, projection data, reconstructed image data, CT image data, information regarding the subject P, imaging conditions, and the like. The memory 41 stores, for example, count data regarding a plurality of energy bins transmitted from the gantry 10. Such data may be stored in an external memory with which the photon counting CT apparatus 1 can communicate instead of the memory 41 (or in addition to the memory 41). The external memory is controlled by a cloud server, for example, when the cloud server that manages the external memory receives a read/write request.

The display 42 displays various types of information. For example, the display 42 displays medical image (CT images) generated by the processing circuitry, graphical user interface (GUI) images and the like for receiving various operations of an operator such as a doctor or a technician. The display 42 is, for example, a liquid crystal display, a cathode ray tube (CRT), an organic electroluminescence (EL) display, or the like. The display 42 may be provided on the gantry 10. The display 42 may be of a desktop type, or may be a display device (for example, a tablet terminal) that can communicate wirelessly with the main body of the console device 40.

The input interface 43 receives various input operations of the operator and outputs an electrical signal indicating the content of a received input operation to the processing circuitry 50. For example, the input interface 43 receives input operations such as collection conditions at the time of collecting detection data or projection data, reconstruction conditions at the time of reconstructing a CT image, image processing conditions at the time of generating a post-processed image from a CT image, and energy bin setting conditions. For example, the input interface 43 is realized by a mouse, a keyboard, a touch panel, a track ball, a switch, a button, a joystick, a camera, an infrared sensor, a microphone, or the like.

The input interface 43 may be provided in the gantry 10. Further, the input interface 43 may be realized by a display device (for example, a tablet terminal) that can communicate wirelessly with the main body of the console device 40. Note that in this specification, the input interface is not limited to one that includes physical operation parts such as a mouse and a keyboard. For example, examples of the input interface include electrical signal processing circuitry that receives an electrical signal corresponding to an input operation from external input equipment provided separately from the device and outputs this electrical signal to a control circuit.

The network connection circuit 44 includes, for example, a network card having a printed circuit board, a wireless communication module, or the like. The network connection circuit 44 implements an information communication protocol depending on the type of network to be connected.

The processing circuitry 50 controls the overall operation of the photon counting CT apparatus 1, the operation of the gantry 10, and the operation of the bed device 30. The processing circuitry 50 executes, for example, a system control function 51, a preprocessing function 52, a reconstruction function 53, an image processing function 54, a scan control function 55, a display control function 56, a pseudo operation control function 57, and the like. These components are realized, for example, by a hardware processor (computer) executing a program (software) stored in the memory 41. The hardware processor is, for example, a CPU, a graphics processing unit (GPU), an ASIC, a programmable logic device (for example, a simple programmable logic device (SPLD) or a complex programmable logic device (CPLD)), a field programmable gate array (FPGA), or the like. The processing circuitry 50 is an example of "second processing circuitry."

The program may be directly incorporated into the circuit of the hardware processor instead of being stored in the memory 41. In this case, the hardware processor realizes the functions by reading and executing the program incorporated into the circuit. The hardware processor is not limited to being configured as a single circuit, but may be configured as one hardware processor by combining a plurality of independent circuits to realize each function. Further, a plurality of components may be integrated into one hardware processor to realize each function.

Each component included in the console device 40 or the processing circuitry 50 may be distributed and realized by a plurality of pieces of hardware. The processing circuitry 50 may be realized by a processing device that can communicate with the console device 40 instead of being a component included in the console device 40. The processing device is, for example, a workstation connected to one X-ray CT apparatus, or a device (e.g., a cloud server) that is connected to a plurality of X-ray CT apparatuses and collectively executes the same processing as the processing circuitry 50 which will be described below.

The system control function 51 controls various functions of the processing circuitry 50 on the basis of input operations received by the input interface 43. The system control function 51 performs, for example, setting of energy bins. The system control function 51 outputs set energy bin setting conditions to the control device 18.

The preprocessing function 52 performs preprocessing such as offset correction processing, inter-channel sensitivity correction processing, and beam hardening correction on detection data output by the DAS 16.

The reconstruction function 53 reconstructs a photon counting CT image regarding the subject P on the basis of detection data (count data). The reconstruction function 53 calculates the amount of X-ray absorption for each of a plurality of base substances on the basis of count data regarding a plurality of energy bins, the energy spectrum of X-rays incident on the subject P, and a response function representing detector response characteristics stored in the memory 41. This processing of obtaining the amount of X-ray absorption for each base substance is also called substance discrimination. Base substances can be set to any substance such as calcium, calcification, bone, fat, muscle, air, organ, lesion, hard tissue, soft tissue, and contrast material. The reconstruction function 53 reconstructs a photon counting CT image representing the spatial distribution of a base substance to be imaged among the plurality of base substances on the basis of the calculated amount of X-ray absorption for each of the plurality of base substances, and stores generated CT image data in the memory 41.

The image processing function 54 converts CT image data into three-dimensional image data or cross-sectional image data of an arbitrary cross section using a known method on the basis of an input operation received by the input interface 43. Conversion into the three-dimensional image data may be performed by the preprocessing function 52.

The scan control function 55 controls detection data collection processing in the gantry 10 by instructing the X-ray high voltage device 14, the DAS 16, the control device 18, and the bed driving device 32. The scan control function 55 controls the operations of each part at the time of capturing for collecting positioning images and at the time of capturing an image used for diagnosis.

The display control function 56 causes the display 42 to display medical images (CT images) generated by the processing circuitry, GUI images for receiving various operations of operators such as a doctor and a technician, and the like.

The pseudo operation control function 57 controls a pseudo operation performed by the detector module 20 (DAS 16). The pseudo operation control function 57 includes, for example, an acquisition function 571, a determination function 572, and a control function 573.

The acquisition function 571 acquires imaging conditions (scan plan) for the subject P input via the input interface 43, for example. The imaging conditions include the magnitude of X-rays (a tube voltage and a tube current), subject information such as the size (weight), age, and sex, and the like of the subject P. Further, the acquisition function 571 acquires the temperature measured by a temperature sensor 15b provided in the X-ray detector 15 (or the DAS 16). The acquisition function 571 is an example of an "acquisition unit."

The determination function 572 calculates the amount of heat generated by the DAS 16 (estimated temperature) during X-ray exposure under the acquired imaging conditions and determines an operation amount of a pseudo operation of the DAS 16 in accordance with the calculated amount of heat generated. Further, the determination function 572 calculates the amount of heat generated by the DAS 16 on the basis of the difference between the acquired temperature of the detector module 20 (the X-ray detector 15 and the DAS 16) and the estimated temperature of the detector module 20 at the time of X-ray exposure, and determines the operation amount of the pseudo operation of the DAS 16 according to the calculated amount of heat generated. The determination function 572 is an example of a "determination unit."

The control function 573 inputs a pseudo operation control signal PS based on the determined operation amount to the DAS 16. The DAS 16 performs the pseudo operation in response to this pseudo operation control signal PS. The control function 573 is an example of a "control unit."

With the above configuration, the photon counting CT apparatus 1 scans the subject P in a scanning manner such as helical scanning, conventional scanning, or step-and-shoot. Helical scanning is a mode in which the subject P is scanned in a spiral manner by rotating the rotating frame 17 while moving the top plate 33. Conventional scanning is a mode in which the rotating frame 17 is rotated in a state in which the top plate 33 is kept stationary to scan the subject P in a circular orbit. Step-and-shoot is a mode in which the position of the top plate 33 is moved at regular intervals to perform conventional scanning in a plurality of scan areas.

[Processing Flow]

[First Processing (Fixed Pseudo Operation)]

Figure 5:
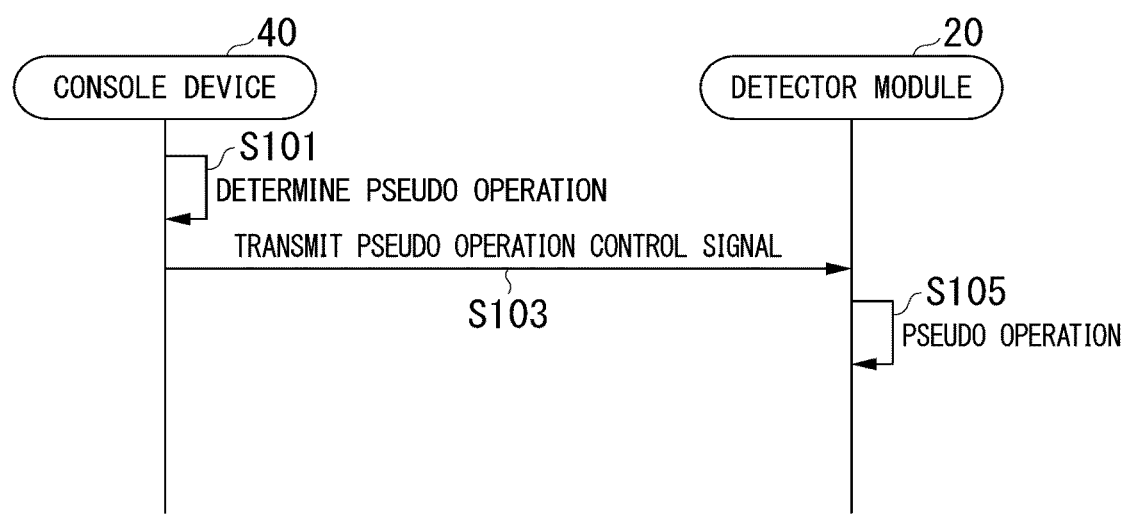
FIG. 5 is a sequence diagram showing an example of a flow of first processing (fixed pseudo operation) of the photon counting CT apparatus 1 according to an embodiment.

Next, an example of pseudo operation processing of the photon counting CT apparatus 1 will be described. FIG. 5 is a sequence diagram showing an example of a flow of first processing (fixed pseudo operation) of the photon counting CT apparatus 1 according to an embodiment. The first processing shown in FIG. 5 is executed when the photon counting CT apparatus 1 is idle.

First, the determination function 572 of the console device 40 determines an operation amount of a pseudo operation of the DAS 16 such that the DAS 16 is maintained at a preset reference temperature (step S101). The reference temperature is, for example, an estimated temperature of the DAS 16 at the time of scanning (at the time of X-ray exposure).

Next, the control function 573 of the console device 40 transmits a pseudo operation control signal PS based on the determined operation amount to the DAS 16 (step S103).

Next, the DAS 16 of the detector module 20 performs a pseudo operation in response to the pseudo operation control signal PS (step S105). By performing the pseudo operation, the DAS 16 can increase the temperature of the X-ray detector 15 (semiconductor detector) during non-scanning (at the time of idle) when there is no exposure with X-rays. Thereafter, at the start of scanning, the DAS 16 stops the pseudo operation. With the above steps, processing of this flowchart ends.

[Second Processing (Changed Pseudo Operation)]

Next, another example of pseudo operation processing of the photon counting CT apparatus 1 will be described. FIG. 6 is a sequence diagram showing an example of a flow of the second processing (changed pseudo operation according to a scan plan) of the photon counting CT apparatus 1 according to an embodiment. The second processing shown in FIG. 6 is executed when the photon counting CT apparatus 1 is idle.

First, the acquisition function 571 of the console device 40 acquires a scan plan for the subject P input by an operator via the input interface 43 (step S201).

Next, the determination function 572 calculates the amount of heat generated by the DAS 16 (for example, the average amount of heat generated) under the acquired imaging conditions (step S203). Next, the determination function 572 determines an operation amount of the pseudo operation of the DAS 16 according to the calculated amount of heat generated (step S205).

Next, the control function 573 of the console device 40 transmits a pseudo operation control signal PS based on the determined operation amount to the DAS 16 (step S207).

Next, the DAS 16 of the detector module 20 performs a pseudo operation in response to the pseudo operation control signal PS (step S209). By performing the pseudo operation, the DAS 16 can increase the temperature of the X-ray detector 15 (semiconductor detector) during non-scanning (at the time of idle) when there is no exposure with X-rays. In the second processing (changed pseudo operation), since the operation amount is determined on the basis of the calculated amount of heat generated according to the imaging conditions, the X-ray detector 15 during non-scanning can be brought closer to the precision during scanning. Thereafter, at the start of scanning, the DAS 16 stops the pseudo operation. With the above steps, the processing of this flowchart ends.

[Third Processing (Changed Pseudo Operation)]

Next, another example of pseudo operation processing of the photon counting CT apparatus 1 will be described. FIG. 7 is a sequence diagram showing an example of a flow of the third processing (changed pseudo operation according to detector temperature) of the photon counting CT apparatus 1 according to an embodiment. The third processing shown in FIG. 7 is executed when the photon counting CT apparatus 1 is idle.

First, the determination function 572 of the console device 40 determines an operation amount of a pseudo operation of the DAS 16 such that the DAS 16 is maintained at a preset reference temperature (step S301).

Next, the control function 573 transmits a pseudo operation control signal PS based on the determined operation amount to the DAS 16 (step S303).

Next, the DAS 16 of the detector module 20 performs a pseudo operation in response to the pseudo operation control signal PS (step S305). By performing the pseudo operation, the DAS 16 can increase the temperature of the X-ray detector 15 (semiconductor detector) during non-scanning (at the time of idle) when there is no exposure with X-rays.

While the DAS 16 performs the pseudo operation, the temperature sensor 15b provided in the detector module 20 (the X-ray detector 15 and the DAS 16) measures the temperature and transmits temperature information to the console device 40 (step S307).

Next, the determination function 572 calculates the amount of heat generated for bringing the temperature of the detector module 20 closer to the temperature at the time of scanning on the basis of the obtained temperature and determines the operation amount of the pseudo operation of the DAS 16 according to the calculated amount of heat generated to adjust the pseudo operation (step S309).

Next, the control function 573 transmits a pseudo operation control signal PS based on the determined operation amount (adjusted operation amount) to the DAS 16 (step S311).

Next, the DAS 16 of the detector module 20 performs a pseudo operation in the adjusted operation amount in response to the pseudo operation control signal PS (step S305). That is, a series of operations performed by the acquisition function 571, the determination function 572, and the control function 573 are repeated until the start of the X-ray exposure. By performing proportional integral differential (PID) control of the temperature of the detector module 20 (the X-ray detector 15 and the DAS 16) and the operation amount of the pseudo operation of the DAS 16, the temperature of detector module 20 during non-scanning can be controlled to approach the temperature at the time of scanning before the start of scanning. Thereafter, at the start of scanning, the DAS 16 stops the pseudo operation. With the above steps, the processing of this flowchart ends.

Modified Example

[Pseudo Operation Control Depending on Shape of X-Ray Detector]

Figure 8:
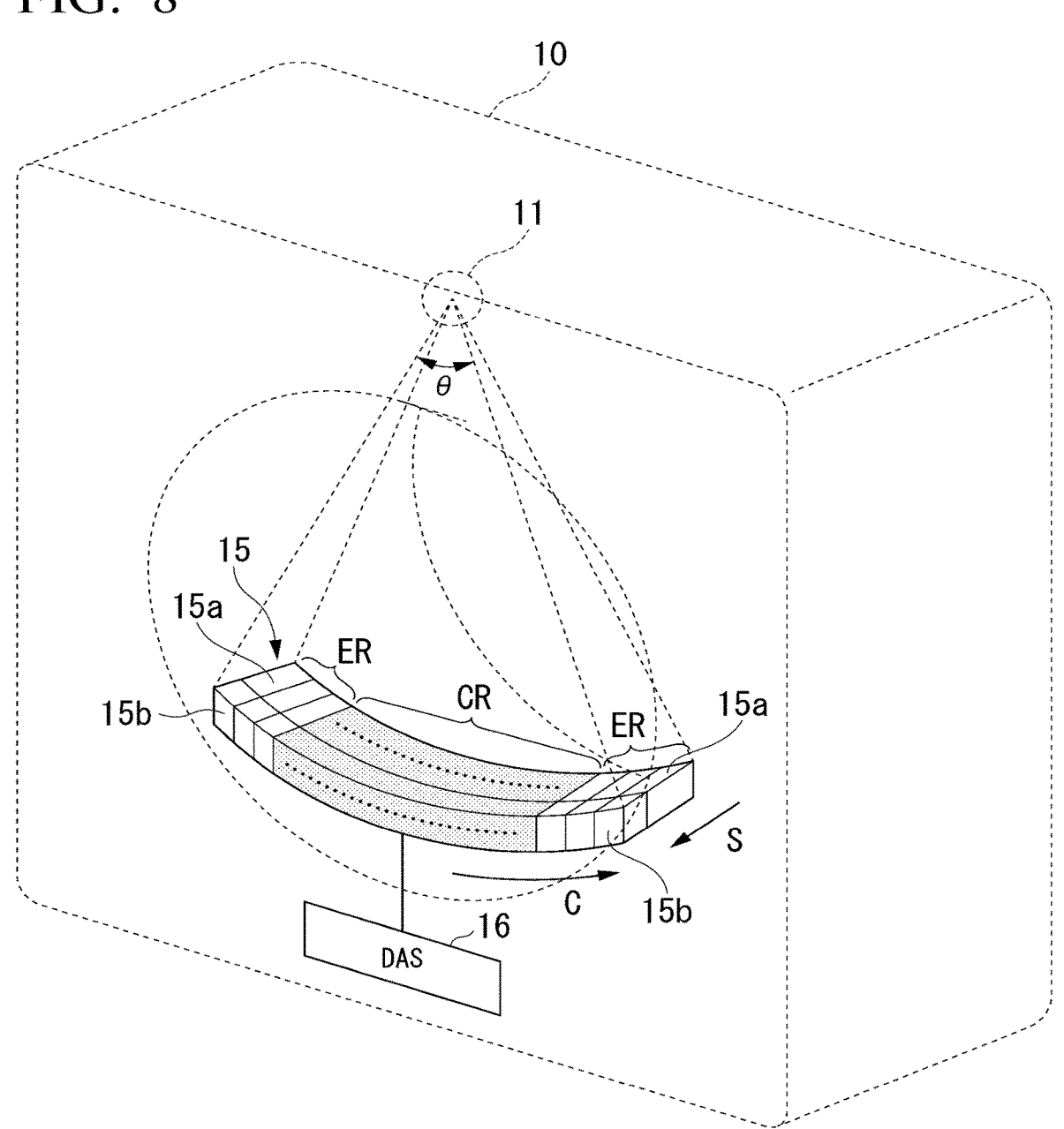
FIG. 8 is a diagram showing heat generation control of the X-ray detector 15 during a pseudo operation according to a modified example.

Next, a modified example will be described. FIG. 8 is a diagram showing heat generation control of the X-ray detector 15 during a pseudo operation according to a modified example. As shown in FIG. 8, a plurality of detection units 15a (pack) are arranged in a channel direction C in the X-ray detector 15. The X-ray dose radiated from the X-ray tube 11 and reaching the X-ray detector 15 during scanning is greater in the detection unit 15a located in the central region CR than in the detection unit 15a located in the edge region ER. Accordingly, temperature increase in the detection unit 15a located in the central region CR becomes greater than temperature increase in the detection unit 15a located in the edge region ER. Considering this difference in the degree of temperature increase, control is performed such that an operation amount of the DAS 16 corresponding to the detection unit 15a located in the central region CR becomes greater than an operation amount of the DAS 16 corresponding to the detection unit 15a located in the edge region ER in the pseudo operation.

[Cooling Device]

As a result of performing the pseudo operation in the detector module 20, the total average temperature of the X-ray detector 15 at the time of idle and scanning increases, and thus there is a concern that the characteristics of the X-ray detector 15 deteriorate or the operating temperature of the X-ray detector 15 reaches the upper limit. For this reason, a cooling device (not shown) is provided in the detector module 20, and the all components in the gantry 10 are controlled to be cooled to be sufficient for stabilizing the temperature of the detector.

[Pseudo Control of Devices Other than DAS 16]

Although the above embodiment describes a configuration in which the DAS 16 of the detector module 20 performs a pseudo operation, the object of the pseudo operation is not limited thereto. Similar pseudo operation control may be performed using a heating element provided near the X-ray detector 15. In this case, temperature control during main scanning can also be performed using a similar method.

According to the embodiment described above, in the photon counting CT apparatus 1 including the detector module 20 having the X-ray detector 15 (semiconductor detector) and the DAS 16 (processing circuitry) that processes detection data detected by the X-ray detector 15, the processing circuitry stabilizes the temperature of the semiconductor detector and improves the accuracy of detection results by generating heat by performing a pseudo operation that operates in a pseudo manner during a period in which X-ray exposure is stopped.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon counting CT apparatus comprising: a detector module including a semiconductor detector; and first processing circuitry configured to process detection data detected by the semiconductor detector, wherein the first processing circuitry is configured to generate heat by performing a pseudo operation during a period in which an X-ray exposure is stopped.

2. The photon counting CT apparatus according to claim 1, wherein the first processing circuitry is configured to perform the pseudo operation to maintain a preset reference temperature.

3. The photon counting CT apparatus according to claim 2, wherein the reference temperature is an estimated temperature of the first processing circuitry at a time of the X-ray exposure.

4. The photon counting CT apparatus according to claim 1, further comprising second processing circuitry configured to:

acquire imaging conditions for a subject;

calculate an amount of heat generated by the first processing circuitry under the acquired imaging conditions;

determine an operation amount of the pseudo operation in accordance with the calculated amount of heat; and input a pseudo operation control signal based on the determined operation amount to the first processing circuitry.

5. The photon counting CT apparatus according to claim 1, further comprising second processing circuitry configured to:

acquire a temperature of the detector module;

calculate an amount of heat generated by the first processing circuitry on the basis of a difference between the acquired temperature and an estimated temperature of the detector module at the time of the X-ray exposure;

determine an operation amount of the pseudo operation in accordance with the calculated amount of heat; and input a pseudo operation control signal based on the determined operation amount to the first processing circuitry.

6. The photon counting CT apparatus according to claim 5, wherein a series of operations performed by the second processing circuitry is repeated until a start of the X-ray exposure.

7. The photon counting CT apparatus according to claim 1, wherein the semiconductor detector includes a plurality of detection units arranged in a channel direction, and wherein an operation amount of the first processing circuitry corresponding to the detection unit located in a central region in the channel direction is controlled to be greater than an operation amount of the first processing circuitry corresponding to the detection unit located in an edge region, among the plurality of detection units.

8. The photon counting CT apparatus according to claim 1, further comprising a cooling device configured to cool the detector module.

9. A photon counting CT apparatus comprising a semiconductor detector and a heating element disposed near the semiconductor detector, wherein the heating element is configured to generate heat by performing a pseudo operation during a period in which an X-ray exposure is stopped.

10. A method of controlling a photon counting CT apparatus comprising a detector module including a semiconductor detector and first processing circuitry configured to process detection data detected by the semiconductor detector, the method comprising causing the first processing circuitry to generate heat by causing the first processing circuitry to perform a pseudo operation during a period in which an X-ray exposure is stopped.

* * * * *